United States Patent [19]

Essig et al.

[11] Patent Number: 5,397,320
[45] Date of Patent: Mar. 14, 1995

[54] DISSECTING SURGICAL DEVICE AND ASSOCIATED METHOD

[76] Inventors: Mitchell N. Essig, 227 High Brook Ct., Pelham, N.Y. 10803; Peter J. Wilk, 185 W. End Ave., New York, N.Y. 10023

[21] Appl. No.: 205,576

[22] Filed: Mar. 3, 1994

[51] Int. Cl.$^6$ .............................................. A61B 17/36
[52] U.S. Cl. ......................................... 606/37; 606/45; 606/47; 606/110; 606/127
[58] Field of Search ................. 606/37, 32, 39, 40, 606/45, 49, 110, 113, 127, 128, 167, 170

[56] References Cited

U.S. PATENT DOCUMENTS

| | | | |
|---|---|---|---|
| 4,503,855 | 3/1985 | Maslanka | 606/47 |
| 4,611,594 | 9/1986 | Grayhack et al. | 606/127 |
| 5,100,423 | 3/1992 | Fearnot | 606/45 X |
| 5,176,688 | 1/1993 | Narayan et al. | 606/127 X |
| 5,190,542 | 3/1993 | Nakao et al. | 606/47 |
| 5,234,439 | 8/1993 | Wilk et al. | 606/127 X |

*Primary Examiner*—Peter A. Aschenbrenner
*Attorney, Agent, or Firm*—R. Neil Sudol; Henry D. Coleman

[57] ABSTRACT

A laparoscopic surgical device comprises an elongate shaft having a plurality of electrically conductive flexible ribs connected to the distal end of the shaft and to one another to form a cage or basket. Upon placement of an organic body in the cage, the ribs are electrically energized. The organic body is pressed against the ribs to dissect the ribs in a single cauterization operation.

18 Claims, 2 Drawing Sheets

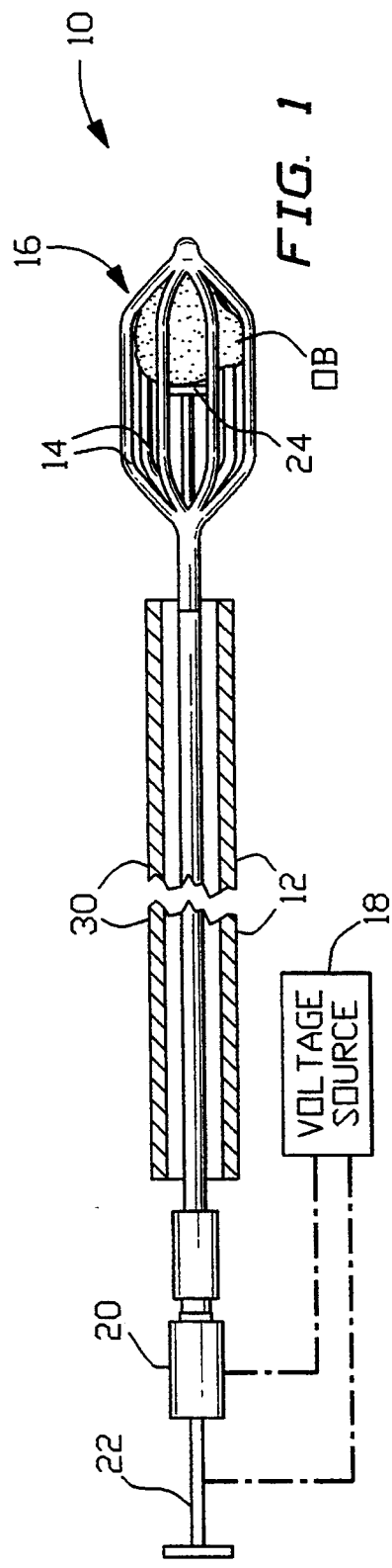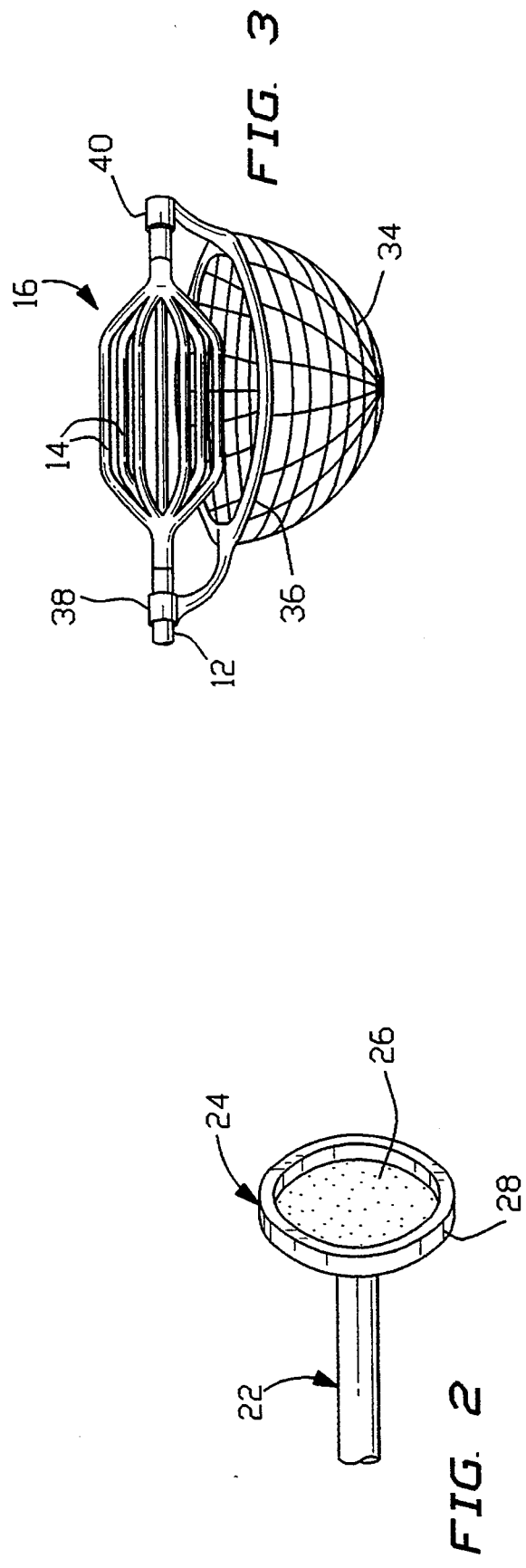

DISSECTING SURGICAL DEVICE AND ASSOCIATED METHOD

BACKGROUND OF THE INVENTION

This invention relates to a surgical instrument or device for dissecting a relatively large organic object into smaller pieces for facilitating removal from the patient. The invention also relates to an associated surgical technique. The instrument and the technique find particular application in laparoscopic surgery.

Laparoscopy involves the piercing of a patient's abdominal wall and the insertion of a cannula through the perforation. Generally, the cannula is a trocar sleeve which surrounds a trocar during an abdomen piercing operation. Upon the formation of the abdominal perforation, the trocar is withdrawn while the sleeve remains traversing the abdominal wall. A laparoscopic instrument, such as a laparoscope or a forceps, is inserted through the cannula so that a distal end of the instrument projects into the abdominal cavity.

Generally, in a laparoscopic surgical procedure, three or four perforations are formed in the abdomen to enable deployment of a sufficient number of laparoscopic instruments to perform the particular surgery being undertaken. Each perforation is formed by a trocar which is surrounded by a sleeve, the sleeves or cannulas all remaining in the abdominal wall during the surgical procedure.

Prior to insertion of the first trocar and its sleeve, a hollow needle is inserted through the abdominal wall to enable pressurization of the abdominal cavity with carbon dioxide. This insufflation procedure distends the abdominal wall, thereby producing a safety space above the patient's abdominal organs. In another, more recently introduced laparoscopic technique, the abdominal wall is lifted mechanically, without insufflation.

Laparoscopic surgery provides several advantages over conventional incision-based surgery. The laparoscopic perforations, in being substantially smaller than the incisions made during conventional operations, are less traumatic to the patient and provide for an accelerated recovery and convalescence. Hospital stays are minimized. Concomitantly, laparoscopic surgery is less time consuming and less expensive than conventional surgery for correcting the same problems.

Laparoscopic surgery is frequently performed to remove a malfunctioning organ such as a gall bladder filled with stones. Generally, a severed bladder is removed from the patient's abdomen by drawing the organ against the distal end of the trocar sleeve and then withdrawing the trocar sleeve with the bladder entrained thereto.

Other organic bodies of substantial size, such as severed myomas, require removal from the abdominal or peritoneal cavity during laparoscopic operations. A myoma is a fibroid mass of tumorous uterine tissue, solid and benign. A myoma can be as large as a baby's head and can squeeze the Fallopian tubes or the uterine cavity, preventing pregnancy. Because a myoma is massive and incompressible, it poses substantial problems in removal from the abdominal cavity via conventional laparoscopic procedures. Unlike a gall bladder, for example, a myoma frequently cannot be simply pulled through a laparoscopic trocar perforation. Moreover, chopping a myoma into smaller tissue parts can cause a significant amount of bleeding.

OBJECTS OF THE INVENTION

An object of the present invention is to provide a surgical device for dissecting an organic body.

Another object of the present invention is to provide such a device wherein the dissecting operation is easy and quick.

Another, more particular, object of the present invention is to provide such a device which can be used in laparoscopic surgery to segment large organic bodies such as myomas.

A further particular object of the present invention is to provide such a device which dissects an organic body with a minimum of bleeding.

Yet another object of the present invention is to provide an associated method for dissecting an organic body.

Another object of the present invention is to provide such a method which is especially useful in laparoscopic surgery.

A further, more specific, object of the present invention is to provide such a method which may be used for dissecting a severed myoma in a laparoscopic operation.

These and other objects of the present invention will be apparent from the drawings and detailed descriptions herein.

SUMMARY OF THE INVENTION

A surgical device comprises, in accordance with the present invention, an elongate shaft having a distal end and a proximal end, a plurality of electrically conductive flexible ribs connected to the distal end of the shaft and to one another to form a cage or basket, and cauterization means, operatively connected to the ribs via the proximal end of the shaft, for electrically energizing the ribs, whereby an organic body inserted between the ribs can be cut into segments.

According to another feature of the present invention, the device further comprises a component coupled to the shaft for forcing the organic body against the ribs during a slicing procedure. That component may take the form of a plunger member slidably inserted through the shaft, the plunger member having a distal end engageable with the organic body for pushing the organic body in a distal direction against the ribs. More specifically, the distal end of the plunger member may be provided with a flange, which serves to increase the area of engagement of the plunger with the organic body during a distally directed stroke of the plunger. The plunger member may additionally be provided at its distal end with an electrode element for conducting current in a bipolar cautery operation through the organic body.

Where the surgical device is used in laparoscopic surgery, it is particularly useful to provide a tubular member slidably disposed about the shaft. The tubular member serves to maintain the cage in a collapsed configuration during insertion thereof through a laparoscopic trocar sleeve.

A surgical method in accordance with the present invention utilizes a surgical device having an elongate shaft provided at a distal end with a plurality of electrically conductive flexible ribs connected to one another to form a cage or basket. The method comprises the steps of (a) inserting the cage into an abdominal cavity of a patient through an opening in an abdominal wall of the patient, (b) placing an organic body into the cage in the abdominal cavity, (c) electrically energizing the ribs, and (d) during the step of electrically energizing and upon placement of the organic body into the cage, forcing the organic body and the cage against one another, thereby slicing the organic body into segments in an electrocautery operation.

The forcing of the organic body and the cage against one another may include the step of pressing the organic body against the ribs, e.g., by a distally directed stroke of a plunger member slidably inserted through the shaft of the device. Where the plunger member is provided at a distal end with an electrode, the method further comprises the step of conducting electrical current through the electrode during the forcing of the organic body and the cage against one another.

According to another feature of the present invention, the cage is inserted in a collapsed configuration into the abdominal cavity. The method then further comprises the step of opening the cage from the collapsed configuration to an opened configuration prior to the placement of the organic body into the cage. The opening of the cage may be implemented automatically owing to an inherent spring bias of the ribs.

In an alternative technique, the cage ribs are closed about the organic body, for instance, by drawing the shaft and the cage in a proximal direction relative to a tubular member surrounding the shaft, thereby urging the ribs towards one another.

A surgical dissecting device in accordance with the present invention is useful in laparoscopic surgery to segment large organic bodies such as myomas. The dissection takes place easily and quickly. In fact, the organic mass is dissected into several segments in a single operation. In addition, the dissection is implemented with a minimum of bleeding.

BRIEF DESCRIPTION OF THE DRAWING

FIG. 1 is a schematic side elevational view, partially broken away, of a laparoscopic dissecting device in accordance with the present invention, showing an organic body deposited in the device for dissection.

FIG. 2 is a partial schematic perspective view of the plunger member of the device of FIG. 1.

FIG. 3 is a schematic side perspective view of a modified laparoscopic dissecting device in accordance with the present invention.

DETAILED DESCRIPTION

Figure 4:
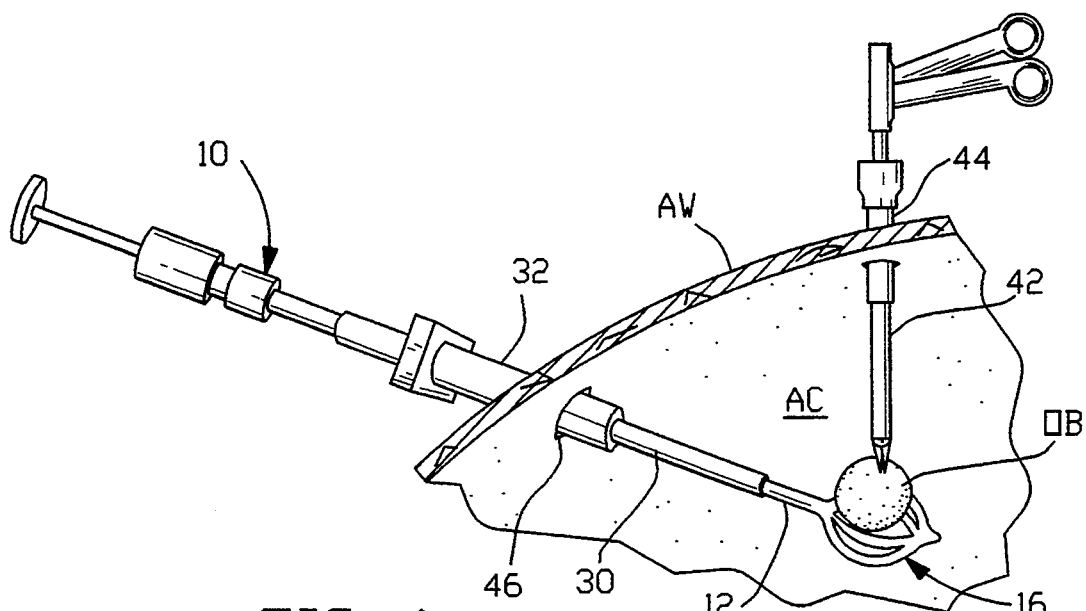
FIG. 4 is a schematic perspective view, with an abdominal wall of a patient broken away, showing a stage in a laparoscopic operation in accordance with the present invention.

As illustrated in FIG. 1, a laparoscopic surgical device 10 comprises an elongate shaft 12 having, at a distal end, a plurality of electrically conductive flexible ribs 14 connected to one another to form a cage or basket 16. A voltage source 18 is operatively connected to ribs 14 via a proximal end 20 of shaft 12 for electrically energizing the ribs, whereby an organic body OB inserted between the ribs can be cut into segments SG (see FIG. 5).

Figure 5:
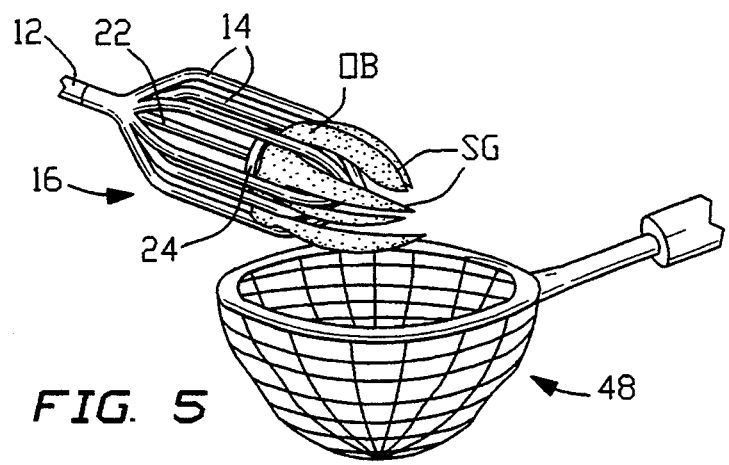
FIG. 5 is a partial schematic perspective view of a laparoscopic instrument in accordance with the present invention, showing a later stage in a laparoscopic operation in accordance with the present invention.

Surgical device 10 further comprises a plunger member 22 slidably coupled to shaft 12 and longitudinally traversing the shaft for forcing organic body OB against ribs 14 during a slicing procedure (see FIG. 5). Plunger member 22 has a flange 24 at a distal end for engaging organic body OB and for pushing the organic body in a distal directon against ribs 14. Flange 24 serves to increase the area of engagement of plunger member 22 with organic body OB during a distally directed stroke of plunger member 22.

As shown in FIG. 2, plunger member 22 is additionally provided at its distal end with an electrode element 26 for conducting current in a bipolar cautery operation through organic body OB. Electrode element 26 is surrounded by a nonconductive rim 28 which insulates the electrode from direct contact with ribs 14 during a dissecting operation. It is to be noted that voltage source 18 may be provided with a safety circuit (not illustrated) for automatically terminating the flow of current to ribs 14 upon a direct electrical contact between the ribs and electrode element 26. Such a circuit is well known in the electrical arts and can be simply provided by any electrical engineer.

As further illustated in FIG. 1, surgical device 10 includes a tubular member 30 through which shaft 12 extends. During insertion of a distal end portion of device 10 through a laparoscopic trocar sleeve 32 (FIG. 4), shaft 12 is withdrawn in a distal direction relative to tubular member 30, whereby cage 16 is retracted inside the distal end of the tubular member. Tubular member 30 thus serves to maintain cage 16 in a collapsed configuration during insertion thereof through trocar sleeve 32. Upon a distally directed stroke of shaft 12 relative to tubular member 30 and the consequent emergence of cage 16 from the tubular member, cage 16 automatically assumes the opened configuration of FIG. 1 owing to the inherent spring bias of ribs 14.

FIG. 3 depicts a modification of surgical device 10. In FIG. 3, those elements identical to corresponding elements in FIG. 1 have been provided with identical reference designations. The embodiment of FIG. 3 differs from the embodiment of FIG. 1 in that a capture net 34 is provided at the distal end of shaft 12. Capture net 34 is attached about a mouth opening to a flexible ring 36, which may be disposed in a collapsed configuration inside tubular member 30 during a laparoscopic deployment procedure. Upon emergence of ring 36 from tubular member 30, ring 36 automatically expands under the action of internal spring forces. Ring 36 is attached to shaft 12 at couplings 38 and 40.

As depicted in FIG. 4, a laparoscopic graspers 42 inserted into an abdominal or peritoneal cavity AC of a patient via a laparoscopic trocar sleeve 44 is used to manipulate organic body OB into cage 16. Device 10 has been inserted into abdominal cavity AC through a perforation 46 in an abdominal wall AW of the patient and more particularly through trocar sleeve 32 which traverses perforation 46.

Upon placement of organic body OB into cage 16 in abdominal cavity AC, ribs 14 are electrically energized by activation of voltage source 18. Then, plunger member 22 is pushed in the distal direction relative to shaft 12 to thereby press organic body OB against ribs 14. This action slices organic body OB into segments SG, as shown in FIG. 5, while simultaneously cauterizing the segments and thereby reducing, if not eliminating, the flow of blood normally incident upon a dissection operation. As illustrated in FIG. 5, a laparoscopic capture pocket 48 may be inserted into the patient's abdominal cavity and held below cage 16 to catch segments SG as they fall upon being formed.

Figure 6:
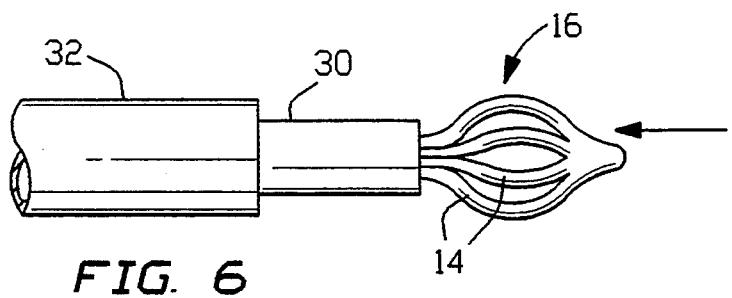
FIG. 6 is a side elevational view of a laparoscopic surgical device in accordance with the present invention, showing an alternative procedure for dissecting an organic body.

As illustrated in FIG. 6, organic body OB and ribs 14 may be forced against one another by an alternative procedure of simply withdrawing cage 16 into the distal end of tubular member 30. This action presses ribs 14 towards one another and into the tissues of organic body OB. Of course, plunger member 22 may be omitted from the device if the rib closure procedure of FIG. 6 is utilized. Organic body OB has been omitted from the drawing in FIG. 6 for purposes of simplicity.

During the step of electrically energizing ribs 14 and the pressing of organic body OB against ribs 14 of cage 16, electrical current is conducted through electrode element 26.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A surgical device comprising:
   an elongate hollow shaft having a distal end and a proximal end;
   a plurality of electrically conductive flexible ribs connected to said distal end of said shaft and to one another to form a cage;
   dissection means, operatively connected to said ribs via said proximal end of said shaft, for electrically energizing said ribs, whereby an organic body inserted between said ribs can be cut into segments; and
   means including a plunger member slidably inserted through said shaft and having a distal and engageable with said organic body for pushing said organic body in a distal direction against said ribs during a slicing procedure.

2. The device defined in claim 1 wherein said plunger member is provided at a distal end with a flange for increasing the area of engagement of said plunger with said organic body during a distally directed stroke of said plunger member.

3. The device defined in claim 1 wherein said plunger member is provided at its distal end with an electrode element for conducting current in a bipolar cautery operation through said organic body.

4. The device defined in claim 1, further comprising a tubular member slidably disposed about said shaft.

5. A surgical method comprising the steps of:
   providing a surgical device having an elongate shaft provided at a distal end with a plurality of electrically conductive flexible ribs connected to one another to form a cage;
   inserting said cage in a collapsed configuration into an abdominal cavity of a patient through an opening in an abdominal wall of the patient;
   upon insertion of said cage into the abdominal cavity of the patient, opening said cage from said collapsed configuration to an opened configuration;
   upon the opening of said cage, placing an organic body into said cage in said abdominal cavity;
   electrically energizing said ribs; and
   during said step of electrically energizing and upon placement of said organic body into said cage, forcing said organic body and said cage against one another, thereby slicing said organic body into segments in an electrocautery operation.

6. The method defined in claim 5 wherein said step of forcing includes the step of pressing said organic body against said ribs.

7. The method defined in claim 6 wherein said shaft is longitudinally traversed by a plunger member, said step of pressing including the step of shifting said plunger member in a distal direction relative to said cage.

8. The method defined in claim 7 wherein said plunger member is provided at a distal end with an electrode, further comprising the step of conducting electrical current through said electrode during said step of forcing.

9. The method defined in claim 5 wherein said step of opening is implemented automatically owing to an inherent spring bias of said ribs.

10. The method defined in claim 9, further comprising the step of disposing a laparoscopic trocar sleeve in said opening, said step of inserting including the step of passing said cage through said trocar sleeve, said step of openig being implemented upon passing of said cage through said trocar sleeve.

11. The method defined in claim 5 wherein said step of forcing includes the step of closing said ribs about said organic body.

12. The method defined in claim 11 wherein said step of closing includes the step of drawing said shaft and said cage in a proximal direction relative to a tubular member surrounding said shaft, thereby urging said ribs towards one another.

13. The method defined in claim 12, further comprising the step of inserting a distal end portion of said tubular member and said cage into a patient's abdominal cavity through a laparoscopic trocar sleeve disposed in an abdominal wall of the patient.

14. The method defined in claim 5, further comprising the step of disposing a laparoscopic trocar sleeve in said opening, said step of inserting including the step of passing said cage through said trocar sleeve.

15. A surgical method comprising the steps of:
   providing a surgical device having an elongate shaft provided at a distal end with a plurality of electrically conductive flexible ribs connected to one another to form a cage;
   inserting said cage into an abdominal cavity of a patient through an opening in an abdominal wall of the patient;
   placing an organic body into said cage in said abdominal cavity;
   electrically energizing said ribs; and
   during said step of electrically energizing and upon placement of said organic body into said cage, forcing said organic body and said cage against one another, thereby slicing said organic body into segments in an electrocautery operation,
   said step of forcing including the step of closing said ribs about said organic body by drawing said shaft and said cage in a proximal direction relative to a tubular member surrounding said shaft, thereby urging said ribs towards one another.

16. The method defined in claim 15, further comprising the step of inserting a distal end portion of said tubular member and said cage into a patient's abdominal cavity through a laparoscopic trocar sleeve disposed in an abdominal wall of the patient.

17. A surgical method comprising the steps of:
providing a surgical device having an elongate hollow shaft provided at a distal end with a plurality of electrically conductive flexible ribs connected to one another to form a cage, said shaft being longitudinally traversed by a plunger member;
inserting said cage into an abdominal cavity of a patient through an opening in an abdominal wall of the patient;
placing an organic body into said cage in said abdominal cavity;
electrically energizing said ribs; and
during said step of electrically energizing and upon placement of said organic body into said cage, forcing said organic body and said cage against one another, thereby slicing said organic body into segments in an electrocautery operation,
said step of forcing including the step of pressing said organic body against said ribs by shifting said plunger member in a distal direction relative to said cage.

18. The method defined in claim 17 wherein said plunger member is provided at a distal end with an electrode, further comprising the step of conducting electrical current through said electrode during said step of forcing.

* * * * *

UNITED STATES PATENT AND TRADEMARK OFFICE
CERTIFICATE OF CORRECTION

PATENT NO. : 5,397,320
DATED : March 14, 1995
INVENTOR(S) : Mitchell N. Essig and Peter J. Wilk It is certified that error appears in the above-indentified patent and that said Letters Patent is hereby corrected as shown below:

Column 5, line 40, claim 1, change "and" (second occurrence) to --end--.

Signed and Sealed this

Twenty-ninth Day of August, 1995

Attest:

BRUCE LEHMAN

Attesting Officer     Commissioner of Patents and Trademarks